United States Patent
Ijpeij et al.

(10) Patent No.: US 7,285,606 B2
(45) Date of Patent: Oct. 23, 2007

(54) PROCESS FOR THE PREPARATION OF A POLYOLEFIN

(75) Inventors: Edwin Ijpeij, Sittard (NL); Henricus Arts, Munstergeleen (NL); Gerardus van Doremaele, Sittard (NL); Felix Beijer, Sittard (NL); Francis van der Burgt, Herten (NL); Martin Zuideveld, Maastricht (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 10/566,840

(22) PCT Filed: Aug. 3, 2004

(86) PCT No.: PCT/EP2004/008709

§ 371 (c)(1),
(2), (4) Date: Jul. 6, 2006

(87) PCT Pub. No.: WO2005/014601

PCT Pub. Date: Feb. 17, 2005

(65) Prior Publication Data

US 2006/0252893 A1 Nov. 9, 2006

(30) Foreign Application Priority Data

Aug. 4, 2003 (EP) .................................. 03077434
Dec. 18, 2003 (EP) .................................. 03078934

(51) Int. Cl.
*C08F 4/60* (2006.01)
(52) U.S. Cl. ...................... 526/136; 526/133; 526/134; 526/160; 526/161; 526/165; 526/172; 502/103; 502/155; 502/157
(58) Field of Classification Search ................ 526/172, 526/160, 161, 165, 133, 134, 136; 502/155, 502/157, 103
See application file for complete search history.

(56) References Cited

U.S. PATENT DOCUMENTS 6,284,700 B1 * 9/2001 Lyu et al. .................... 502/152
6,316,663 B1 * 11/2001 Guram et al. ................ 560/210
6,750,345 B2 * 6/2004 Boussie et al. ............... 546/10

* cited by examiner

*Primary Examiner*—Caixia Lu
(74) *Attorney, Agent, or Firm*—Nixon & Vanderhye P.C.

(57) ABSTRACT

The invention related to a process for the polymerization of at least one aliphatic or aromatic hydrocarbyl C2-20 mono- or multiolefin in the presence of a catalyst and a boron comprising co-catalyst, wherein the catalyst comprises a composition of a metal-organic reagent, a spectator ligand and optionally at least one equivalent of a hydrocarbylating agent. The invention further relates to a polymer obtainable by the process of the invention.

12 Claims, No Drawings

PROCESS FOR THE PREPARATION OF A POLYOLEFIN

This application is the US national phase of international application PCT/EP2004/008709 filed 3 Aug. 2004 which designated the U.S. and claims benefit of EP 03077434.3, dated 4 Aug. 2003 and EP 03078934.1, dated 18 Dec. 2003, the entire content of which is hereby incorporated by reference.

The invention relates to a process for the preparation of a polymer of at least one aliphatic or aromatic hydrocarbyl $C_{2-20}$ mono- or multiolefin in the presence of a catalyst and a boron comprising co-catalyst.

Such a process is described in WO 98/49212.

WO 98/49212 describes the preparation of a polymer of one or more aliphatic or aromatic hydrocarbyl $C_{2-20}$ mono- or diolefins in the presence of a catalyst consisting of a metal-organic compound and a boron comprising co-catalyst. A boron comprising co-catalyst is used because of the high reactivity of the catalyst system described in WO 98/49212 in combination with a boron comprising co-catalyst.

Disadvantage of the process described in WO 98/49212 is the use of an expensive catalyst, which requires several reaction steps for its production. These processes require at least four steps: (i) reaction of a ligand with a strong base resulting in a metal-organic salt of this ligand, followed by (ii) contacting this salt with a metal-organic reagent resulting in a metal-organic compound which has to (iii) be hydrocarbylated and (iv) further contacted with a borane or borate in order to form the active species. For some catalysts an additional oxidation step after the formation of the metal-organic compound is needed using an oxidizing agent.

An aim of the invention is to provide a process for the preparation of a polymer comprising one or more aliphatic or aromatic hydrocarbyl $C_{2-20}$ mono- or multiolefins in the presence of a boron comprising co-catalyst and a catalyst, which can be formed in situ in the polymerization equipment.

This aim is achieved in the process of the invention by a catalyst, which comprises a composition of a spectator ligand, a metal-organic reagent, and optionally at least one equivalent of a hydrocarbylating agent.

By the process of the invention a polymerization of one or more aliphatic or aromatic hydrocarbyl $C_{2-20}$ mono- or multiolefins in the presence of a boron comprising co-catalyst can be carried out in the presence of a catalyst, which is formed in situ in the polymerization equipment.

Processes for the preparation of a polymer of at least one aliphatic or aromatic hydrocarbyl $C_{2-20}$ mono- or multiolefins are fairly well known in the art. These processes are generally conducted by contacting at least one mono-, or multiolefinic monomer with a catalyst in the presence of an inert hydrocarbon solvent. Examples of an inert hydrocarbon solvent are a $C_{5-12}$ hydrocarbon which may be substituted by an $C_{1-4}$ alkyl group, such as pentane, hexane, heptane, octane, cyclohexane, methylcyclohexane and hydrogenated naphta. The process of the invention may be conducted at temperatures from about 20° C. to about 250° C., depending on the product being made.

A mono-olefinic monomer is understood to be a molecule containing a polymerizable double bond, optionally containing a polar functional group. A multiolefinic monomer is understood to be a molecule containing at least two polymerizable double bonds, optionally containing also a polar fuctional group.

Suitable mono-olefin monomers may be ethylene or $C_{3-20}$ monoolefins. Preferred monomers include ethylene and $C_{3-12}$ alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, $C_{4-12}$ straight chained or cyclic hydrocarbyl radicals which are unsubstituted or substituted by a $C_{1-4}$ alkyl radical. Illustrative non-limiting examples of such alpha-olefins are one or more of propylene, 1-butene, 1-pentene, 1-hexene, 1-octene, and 1-decene, styrene, alpha methyl styrene, p-t-butyl styrene, and the cyclic olefins such as cyclobutene, cyclopentene, norbornene, alkyl-substituted norbornenes, Suitable multiolefins include $C_4$-$C_{35}$ multiolefins. The double bonds may be conjugated or not conjugated, endo- and or exocyclic and may have different amounts and type of substituents. Examples of such multiolefins include 1,3-butadiene, isoprene, 1,4-hexadiene or 1,6-octadiene, divinylbenzene; monocyclic or polycyclic dienes, for example 1,4-cyclohexadiene, alkenyl-substituted norbornenes and the like (e.g. 5-methylene-2-norbornene and 5-ethylidene-2-norbornene, 5-vinylnorbornene, and bicyclo-(2,2,1)-hepta-2,5-diene), dicyclopentadiene, vinylcyclohexene and the like.

Homo-, co- and ter-polymers of the above mentioned mono- and multimonomers and blends thereof can be prepared with the present invention.

Other olefin polymers which may be prepared in accordance with the present invention may be determined by one of ordinary skill in the art using non-inventive testing.

In the process of the invention a boron comprising co-catalyst is used. A boron comprising co-catalyst is understood to be a cocatalyst as described in *Chem. Rev.*, 2000, 100, 1391 by E. Y-X. Chen and T. J. Marks.

In the process of the invention the metal-organic reagent can be represented by formula 1:

$$ML_jX_p \qquad \text{(formula 1)}$$

with M being a metal from group 3-11, X a monoanionic ligand bonded to M, L a neutral Lewis basic ligand bonded to M, j representing an integer denoting the number of neutral ligands L and p is the valency of the metal M.

Examples of Lewis basic ligands include ethers, such as tetrahydrofuran (THF), diethylether, thioethers, like thiophene, diethylsulfide, dimethylsulfide, .amines, such as trialkylamines, pyridine, bipyridine, TMEDA, (−)-sparteine), phosphanes and diphosphanes, such as triphenylphoshine, trialkylphosphanes, bidentate alkyl or aryldiphosphanes). The amount of ligands (X and L) depends on the valency of the metal and the stability of the metal-organic reagent. The metal-organic reagent may be monomeric, oligomeric or a cluster. The number of anionic ligands equals the valency of the metal used. The number of neutral ligands on the metal-organic reagent may range from 0 to the amount that satisfies the 18-electron rule, as known in the art.

Each anionic ligand, X, may be independently selected from the group consisting of monoanionic spectator ligands, hydride, halide, alkyl, silyl, germyl, aryl, amide, aryloxy, alkoxy, phosphide, sulfide, acyl, pseudo halides such as cyanide, azide, acetylacetonate, etc., or a combination thereof. Preferably, X is hydride or a moiety selected from the group consisting of monoanionic spectator ligands, halide, alkyl, aryl, silyl, germyl, aryloxy, alkoxy, amide, siloxy and combinations thereof (e.g. alkaryl, aralkyl, silyl substituted alkyl, silyl substituted aryl, aryloxyalkyl, aryloxyaryl, alkoxyalkyl, alkoxyaryl, amidoalkyl, amidoaryl, siloxyalkyl, siloxyaryl, amidosiloxyalkyl, haloalkyl, haloaryl, etc.) having up to 20 non-hydrogen atoms.

The process of the invention is optionally carried out in the presence of at least one equivalent of an hydrocarbylating agent. In the process of the invention hydrocarbylating agents are nucleophilic groups comprising a metal-, or a metalloid-carbon or hydride bond, which are able to substitute an X from an MX bond. The number of equivalents required for the process of the invention depends on the amount and the type (mono-, or dianionic) of the spectator ligand.

Examples of hydrocarbylating agents are: tri-, or tetrahydrocarbyl boron, tri-, or tetrahydrocarbyl aluminium, tri-, or tetrahydrocarbyl gallium, tri-, or tetrahydrocarbyl indium and di-, or tetrahydrocarbyl tin, or the reaction products of these hydrocarbylating agents with sterically hindered alcohols, thiols, amines or phosphanes.

Preferably the hydrocarbylating agent comprises a metal or a metalloid chosen from group 1, 2, 11, 12, 13 or 14. Examples of hydrides from metals or metalloids of group 1, 2, 11, 12, 13, 14 include: lithiumhydride, sodiumhydride, potassiumhydride, calciumhydride, magnesiumhydride, copperhydride, zinchydride, cadmiumhydride, borane, aluminumhydride, galliumhydride, siliconhydride, germaniumhydride, and tinhydride.

Preferably the hydrocarbylating agent comprises Li, Mg, Zn, or Al.

Examples of Li comprising hydrocarbylating agents are methyllithium, phenyllithium, benzyllithium, biphenyllithium, naphtyllithium, lithio-dimethylresorcinol, and lithio-N,N-dimethylaniline.

Examples of magnesium comprising hydrocarbylating agents are methylmagnesiumhalide, phenylmagnesiumhalide, benzylmagnesiumhalide, biphenylmagnesiumhalide, naphtylmagnesiumhalide, tolylmagnesiumhalide, xylylmagnesiumhalide, mesitylmagnesiumhalide, dimethylresorcinolmagnesiumhalide, N,N-dimethylanilinemagnesiumhalide, dimethylmagnesium, diphenylmagnesium, dibenzylmagnesium, (biphenylene)magnesium, dinaphtylmagnesium, ditolylmagnesium, dixylylmagnesium, dimesitylmagnesium, bis(dimethylresorcinol)magnesium, and bis(N,N-dimethylaniline)magnesium.

Examples of aluminium comprising hydrocarbylating agents are diisobutylaluminium hydride, $C_{1}$-$C_{20}$ trihydrocarbyl aluminium, and hydrocarbylaluminoxanes.

To facilitate the process of the invention, the process may be carried out in the presence of a base other than a hydrocarbylating agent. Examples of such bases include, amines, phosphanes, carboxylates (for example potassium acetate), hydroxides, cyanides, amides and carbonates of Li, Na, K, Rb, Cs, ammonium and the group 2 metals Mg, Ca, and Ba, the alkali metal (Li, Na, K, Rb, Cs) phosphates and the phosphate esters (eg. $C_6H_5$ $OP(O)(ONa)_2$ and related aryl and alkyl compounds) and their alkoxides and phenoxides, thallium hydroxide, alkylammonium hydroxides, hydrides of from metals or metalloids of group 1, 2, 11, 12, 13, 14. Also the metallic alkalimetals of group 1 may be applied as a base.

In the process of the invention a spectator ligand is chosen from a monoacidic spectator ligand, a diacidic bidentate spectator ligand, a monoacidic bidentate spectator ligand, or a Lewis basic bi-, or multidentate spectator ligand.

An example of a mono acidic spectator ligand is an imine ligand according to formula 2, or the HA adduct thereof, wherein HA represents an acid, of which H represents its proton and A its conjugate base, $$Y=N-R \quad \text{(formula 2)},$$

wherein Y is selected from a substituted carbon, nitrogen or phosphorous atom and R represents a substituent. If Y represents a substituted carbon atom, the number of substituents is 2. If Y represents a substituted nitrogen atom, the number of substituents is 1 and the number of substituents is 1 or 3 if Y represents a phosphorous atom, depending on the valency of the phosphorous atom.

Substituents on carbon, nitrogen or phosphorous may be equal or different, optionally linked with each other, optionally having hetero atoms. Substituents may be protic or aprotic.

A protic substituent is defined here as a substituent which has at least one group 15 or group 16 atom containing at least one proton.

Examples of protic subsituents include $C_1$-$C_{20}$ linear, branched or cyclic hydrocarbyl radicals, substituted with a group 15 or 16 atom bearing at least one hydrogen atom. Preferred protic substituents include phenolic radicals, pyrrolic radicals, indolic radicals, and imidazolic radicals.

The substituent is called aprotic if the substituent lacks a group containing a group 15 or group 16 atom bearing a proton. An unsubstituted aprotic hydrocarbyl radical can be a $C_1$-$C_{20}$ linear, branched or cyclic radical, a hydrogen atom, a halogen atom, a group 14 oxy radical—such as a $C_{1-8}$ alkoxy radical, a $C_{6-10}$ aryl or aryloxy radical, silyloxy radical, germanyloxy radical, stannyloxy radical—an amido radical, or a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula:

(formula 3)

or a germanyl radical of the formula:

(formula 4)

wherein $R^{2j}$ with j=1 to 3 is independently selected from the group consisting of hydrogen, a $C_{1-8}$ alkyl or alkoxy radical, $C_{6-10}$ aryl, aryloxy radicals a silyl radical of formula 3 or a germanyl radical of formula 4, each substituent $R^{2j}$ may be linked with another $R^{2j}$ to form a ring system.

The substituent R can be H, or being equal as these for the substituent on Y.

Examples of imine ligands according to formula (2) include: guanidines, iminoimidazolines, phosphinimines, phenolimines, pyrroleimines, indoleimines and imidazoleimines.

R may be linked with Y, thus forming a ring system, optionally comprising hetero atoms, or optionally comprising functional groups. Examples of ligands comprising such ring systems include: 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

In the process of the invention, HA represents an acid, of which H represents its proton and A its conjugate base. Examples of A are halogenides, (such as fluoride, chloride, bromide, or iodide), sulfate, hydrogensulfate, phosphate, hydrogenphosphate, dihydrogenphosphate, carbonate, hydrogencarbonate, aromatic or aliphatic carboxylates, cyanide, tetrafluoroborate, (substituted) tetraphenylborates, fluorinated tetraarylborates, alkyl or aryl sulfonates.

In case the HA adduct of the imine ligand is used, one more equivalent of the hydrocarbylating agent is required.

Examples of mono- or diacidic spectator ligand are ligands according to formula 5:

(formula 5), wherein $A_1$ and $A_2$ are monoacidic cyclopentadienyl comprising ligands (Cp), with q and r representing an integer denoting the number of Cp ligands with q+r=1 or 2, optionally linked by n bridging groups Z, with n representing the number of parallel bridges Z, $A_1$, $A_2$ when bonded via Z together forming a bidentate diacidic spectator ligand or if Z is absent $A_1$, $A_2$ form two monoacidic spectator ligands.

The ligands $A_1$ and $A_2$ are defined as cyclopentadienyl comprising ligands. Under cyclopentadienyl comprising ligands is understood that a part of the molecular structure contains a cyclopentadienyl (Cp) ring. This ring may be substituted with at least one R'-group. When the Cp-ring is substituted with at least two R' groups, these R' groups may form ring systems. As result of that the Cp-comprising ligand may be indenyl comprising ligands or fluorenyl comprising ligands. The ligands $A_1$ and $A_2$ may be each independently selected (substituted) cyclopentadienyl groups, (substituted) indenyl groups, (substituted)fluorenyl groups, (substituted) tetrahydroindenyl groups, (substituted) tetrahydrofluorenyl groups, (substituted) octahydrofluorenyl groups, (substituted) benzoindenyl groups, (substituted) heterocyclopentadienyl groups, (substituted) heteroindenyl groups, (substituted) heterofluorenyl groups, or its isomers. Here and in the following a hetero cyclopentadienyl group (in the following also referred to as 'hetero ligand') is understood to be a group that has been derived from a cyclopentadienyl group, but in which at least one of the C atoms in the 5-ring of the cyclopentadienyl has been replaced by a hetero atom, which hetero atom may be chosen from group 14, 15 or 16. If there is more than one hetero atom present in the 5-ring of the hetero ligand, these hetero atoms may be either the same or different. More preferably, the hetero atom has been chosen from group 15, while yet more preferably the hetero atom is phosphorus.

The R' groups may each independently be hydrogen or a hydrocarbon radical with 1-20 carbon atoms (e.g alkyl, aryl, biaryl, aralkyl, alkaryl and the like) or a heteroatom comprising moiety from group 13-17. Examples of such hydrocarbon radicals are methyl, ethyl, n-propyl, i-propyl, butyl (including isomers), hexyl (including isomers), decyl (including isomers), phenyl, biphenyl (including isomers) and the like. Examples of heteroatom comprising moieties of group 13-17 include borane radicals, silyl radicals, germyl radicals, stannyl radicals, amide radicals, phosphide radicals, oxide radicals, sulphide radicals, halide radicals, halide substituted hydrocarbyl radicals and the like. Also, two adjacent hydrocarbon radicals may be connected with each other in a ring system. Such a group as well may contain one or more R' groups as substituents. R' may also be a substituent which instead of or in addition to carbon and/or hydrogen may comprise one or more hetero atoms of groups 13-17.

The bridging group Z may contain $sp^3$, $sp^2$ or sp hybridized atoms of group 13 to 16 or combinations thereof. The bridging group Z may consist of linear, cyclic fragments, spiro ring systems, or combinations thereof. Examples of a carbon containing Z group may each separately be a hydrocarbon group with 1-20 carbon atoms, e.g. alkylidene, arylene, biarylene, aryl alkylidene, etc. Examples of such groups are methylene, ethylene, propylene, butylene, phenylene, naphtylene, biphenylene, binaphtylene. Examples of silicium containing groups are dimethylsilyl, diethylsilyl, dipropylsilyl, including its isomers, (substituted) diphenylsilyl, dimethoxysilyl, diethoxysilyl, dipropoxysilyl, and diphenoxysilyl.

An example of a diacidic bidentate spectator ligand or a monoacidic bidentate spectator ligand is a ligand according to formula 6:

(formula 6)

in which $A_1$ is a delocalized $\eta^5$ bonding cyclopentadienyl comprising ligand, Z is a moiety comprising boron, or a member of Group 14, and optionally also sulfur or oxygen, said moiety having up to 20 non-hydrogen atoms, and optionally $A_1$ and Z together form a fused ring system, D is a Lewis basic ligand bonded to Z comprising a group 15 or 16 atom having up to 20 non-hydrogen atoms, optionally D and Z together form a fused ring system and b=0 or 1. Hereinafter a Lewis basic ligand is also refered to as a donor moiety. The mono-, or diacidic spectator ligand has 1 or 2 acidic protons, one of which is the acidic cyclopentadienyl proton. If the acidic spectator ligand contains only 1 proton (thus the cyclopentadienyl acidic proton), then b equals 0 and D is a neutral two electron donor moiety. If the acidic spectator ligand contains 2 protons, than b equals 1 and D contains an acidic proton.

Preferably D is —O—, —S—, —NR*—, —PR*—, or a neutral two electron donor moiety selected from the group consisting of OR*, SR*, NR*$_2$, or PR*$_2$.

Z may be SiR*$_2$, CR*$_2$, SiR*$_2$SiR*$_2$, CR*$_2$CR*$_2$, CR*=CR*, CR*$_2$SiR*$_2$, GeR*$_2$, BR*, BR*$_2$; wherein each R* can be independently selected from the group consisting of hydrogen, alkyl, aryl, silyl, halogenated alkyl, halogenated aryl radicals, or combinations thereof (e.g. aralkyl, alkaryl, haloalkaryl and haloaralkyl radicals) having up to 20 non-hydrogen atoms, or two or more R* groups from Y, Z, or both Y and Z form a fused ring system.

Another example of a monoacidic bidentate ligand (SH) is a) is a bi- or multidentate ligand, wherein S is represented by formula 7:

(formula 7)

with,

Y represents an anionic moiety of S, Z optional bridging groups between the Y moiety and the DR'$_n$ and/or Ar group, D a hetero atom chosen form group 15 or 16, R' an optional substituent, Ar an electron-donating aryl group, n the number of R' groups bonded to D, and q and s are integers with q+s≧1.

If the ligand is a ligand represented by (Ar-Z-)$_s$Y(-Z-DR'$_n$)$_q$, the transition metal is preferably chosen from groups 4-6 of the Periodic Table of the Elements. More preferably, the transition metal has been chosen from group 4, with the most preference to titanium (Ti) as transition metal. The transition metal is preferably present in reduced form in the compound, which means that the transition metal is in a reduced oxidation state (p). By 'reduced oxidation state' is meant an oxidation state which is lower than the highest possible oxidation state for a particular metal, which means at most $M^{3+}$ for a transition metal of group 4, at most $M^{4+}$ for a transition metal of group 5 and at most $M^{5+}$ for a transition metal of group 6.

Examples of Y moieties include hydrocarbyl substituted groups comprising a group 15 or 16 atom, (substituted) cyclopentadienyl, (substituted) indenyl, (substituted) fluorenyl, (substituted) heterocyclopentadienyl, (substituted) heteroindenyl, (substituted) heterofluorenyl, or imine groups. Imine groups are defined as groups containing a double bonded nitrogen atom. Examples of imine groups are ketimide, guanidine, phosphinimide, iminoimidazoline, (hetero)aryloxyimines, pyrroleimines, indoleimines, imidazoleimines or (hetero)aryloxides, (substituted) pyridin-2-yl-methoxy, (substituted) quinolin-2-yl-methoxy, 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole, and the like.

The optional bridging group Z may contain $sp^3$, $sp^2$ or sp hybridized atoms or combinations thereof. The bridging group Z may consist of linear, cyclic fragments, or combinations thereof. The Z groups may each separately be a hydrocarbon group with 1-20 carbon atoms, e.g. alkylidene, arylene, aryl alkylidene, etc. Examples of such groups are methylene, ethylene, propylene, butylene, biphenylene, binaphtylene, phenylene, whether or not with a substituted side chain, linear or cyclic.

Besides carbon, the main chain of the Z group may also contain larger members of group 14, such as silicon, germanium or tin. Examples of such Z groups are: dialkyl silylene, dialkyl germylene, tetra-alkyl disilylene or tetraalkyl silaethylene ($—SiR'_2CR'_2$).

The hetero atom containing donor group $DR'_n$ consists of at least one group 15 or group 16 atom, or a combination thereof. Examples of donor groups include imine groups as defined above, amine groups, phosphane groups, ether groups, or thioether groups.

Also, Y, Z and D may be part of an aromatic ring system, optionally containing $sp^3$, $sp^2$ or sp hybridized atoms or combinations thereof, together forming a spectator ligand. The D atom may thus be a part of the bridging group. In this case, the D atom containing bridging group may be further substituted by at least one optional bridging group Z containing donor groups $DR'_n$. Examples of spectator ligands containing aromatic ring systems having a donor atom D in the bridging group Z include (hetero)aryloxyimines, pyrroleimines, indoleimines, imidazoleimines or (hetero)aryloxides, (substituted) pyridin-2-yl-methoxy, (substituted) quinolin-2-yl-methoxy, 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

Preferably, the Y moiety may be an amido (—NR'—) group, a phosphido (—PR'—) group, an imine group, a (substituted) cyclopentadienyl group, a (substituted) indenyl group, a (substituted) group, a fluorenyl group, a (substituted) heterocyclopentadienyl group, a (substituted) heteroindenyl group, and a (substituted) heterofluorenyl group, Here and in the following a hetero cyclopentadienyl group (in the following also referred to as 'hetero ligand') is understood to be a group that has been derived from a cyclopentadienyl group, but in which at least one of the C atoms in the 5-ring of the cyclopentadienyl has been replaced by a hetero atom, which hetero atom may be chosen from group 14, 15 or 16 of the Periodic Table of the Elements. If there is more than one hetero atom present in the 5-ring of the hetero ligand, these hetero atoms may be either the same or different. More preferably, the hetero atom has been chosen from group 15, while yet more preferably the hetero atom is phosphorus.

Preferably, the electron donor group $DR'_n$ consists of a hetero atom D, chosen from group 15 or 16, and one or more substituents R' bonded to D. The number of R' groups is linked up with the nature of the hetero atom D, in the sense that n=2 if D is from group 15 and n=1 if D is from group 16. The substituent R' bonded to D is as defined. The hetero atom D has preferably been chosen from the group comprising nitrogen (N), oxygen (O), phosphorus (P) and sulphur (S); more preferably, the hetero atom is nitrogen (N) or phosphorus (P). It is further possible for two R' groups in the $DR'_n$ group to be connected with each other to form a ring-shaped structure (so that the DR' group can be a pyrrolidinyl group). The DR', group can form coordinative bonds with M.

The aromatic electron-donating group (or donor), Ar, used can be substituted or non-substituted aryl group ($C_6R'_5$), such as phenyl, tolyl, xylyl, mesitylyl, cumyl, tetramethyl phenyl, pentamethyl phenyl, etc. The Ar group may also contain at least one heteroatom from group 15 or group 16. Examples of such heteroatom containing Ar groups are (substituted) pyrrole, (substituted) pyridine, (substituted) thiophene, (substituted) furan. The coordination of this Ar or heteroatom containing Ar group in relation to M may vary from $\eta^1$ to $\eta^6$.

The R' groups may each separately be hydrogen or a hydrocarbon radical with 1-20 carbon atoms (e.g alkyl, aryl, aryl alkyl and the like). Examples of such hydrocarbon radicals are methyl, ethyl, propyl, butyl, hexyl, decyl, phenyl and the like. Also, two adjacent hydrocarbon radicals may be connected with each other in a ring system. As result from that, the Cp group may be an indenyl, tetrahydroindenyl, a fluorenyl, a tetrahydrofluorenyl, an octahydrofluorenyl or a benzoindenyl group. Such a group as well may contain one or more R' groups as substituents. R' may also be a substituent which instead of or in addition to carbon and/or hydrogen may comprise one or more hetero atoms of groups 14-16. Thus, a substituent may be a Si-containing group.

An example of a Lewis basic bi- or multidentate ligand is a ligand according to formula 8:

(formula 8)

wherein Z is a bridging group, between two donor atom containing groups (D),

D a group comprising a hetero atom chosen from group 15 or 16, and R is a substituent. For all clarity, the ligand of formula 8 is not the same ligand as the ligand (L) in the metal-organic reagent. Examples of a Lewis basic bi-, or multidentate ligand are di-imines, tri-imines and di-imines comprising an aromatic group comprising a hetero atom of group 15 or 16.

If a ligand according to formula 8 is used, the metal of the metal-organic reagent preferably is a metal from group 7-11.

The process of the invention can be carried out in a broad variety of polymerization equipment. It can be carried out in a single reactor, or in multiple reactors, in series or parallel and combinations thereof. The process can be carried out in gasphase, bulk, or in suspension/slurry as a batch or continuous process.

The process of the invention is preferably carried out in a solvent. Suitable solvents are solvents that do not react with the metal-organic reagent or the metal-organic compound formed in the process of the invention. Examples of suitable solvents include aromatic and aliphatic hydrocarbons, halogenated hydrocarbons, or mixtures thereof.

The process of the invention can be carried out in different ways, which can be distinguished by the sequence in which the spectator ligand, the metal-organic reagent, the hydrocarbylating agent and the boron comprising co-catalyst are added to a polymerization reactor. Preferably the spectator ligand, the metal-organic reagent, the hydrocarbylating agent and the boron comprising co-catalyst are each added as a solution or a suspension to the process of the invention.

One way is to add the spectator ligand, the metal-organic reagent, the hydrocarbylating agent and the boron comprising co-catalyst directly to the polymerization reactor.

Another way is that the spectator ligand, the metal-organic reagent and the hydrocarbylating agent are premixed before the reactor. The advantage of premixing the spectator ligand, the metal-organic reagent and the hydrocarbylating agent is that this can be done under conditions of temperature and time different from those in the polymerization reactor, thus leading to a more active catalyst.

In this way the boron comprising co-catalyst can be added to the thus formed mixture either before the reactor or parallel to this mixture direct into the reactor. Adding the boron comprising co-catalyst to the above mentioned premixture has the advantage that an active catalyst system can be formed in a more concentrated environment than in the reactor. An even more active catalyst can be obtained by mixing the metal-organic reagent with the spectator ligand before the addition of the hydrocarbylating agent.

The invention is further related to a polymer obtainable with the process of the invention and in particular obtainable with a process using a spectator ligand $(Ar-Z-)_sY(-Z-DR'_n)_q$, wherein Z is an optional bridging groups between an anionic moiety Y and the $DR'_n$ and/or Ar group, D a hetero atom chosen form group 15 or 16, R' an optional substituent, Ar an electron-donating aryl group, n the number of R' groups bonded to D, q and s integers with $q+s \geq 1$ and wherein Y is an imine group. Preferably the imine is a ketimide, phosphinimide, guanidine, or iminoimidazoline. Other preferred imines are spectator ligands wherein Y, R and D are part of an aromatic ring system, optionally containing $sp^3$, $sp^2$ or sp hybridized atoms or combinations thereof. Examples of these imines include: (hetero)aryloxyimine (like (substituted) derivatives of phenoxyimines, pyrroleimines, hydroyquinolines and the like) (hetero)arylsulphidoimine, (hetero)arylphosphidoimine and (hetero)arylamidoimine.

The invention also relates to a polymer obtainable with the process of the invention wherein Y is an imine and wherein the donor D is a ketimine, phosphinimine, guanidine, or iminoimidazoline.

The invention further relates to a polymer obtainable with the process of the invention using a spectator ligand $(Ar-Z-)_sY(-Z-DR'_n)_q$, wherein Y represents an anionic moiety of S, Z is an optional bridging groups between the Y moiety and the $DR'_n$ and/or Ar group, D a hetero atom chosen form group 15 or 16, R' an optional substituent, Ar an electron-donating aryl group, n the number of R' groups bonded to D, q and s integers with $q+s \geq 1$ and, and wherein D is a ketimide, phosphinimide, guanidine, or an iminoimidazoline.

Polymerisation Equipment.

The batch copolymerisation was carried out in a polymerisation equipment, having a catalyst dosing vessel equipped with a catalyst dosing pump for the addition of the catalyst to a 2-liter batch autoclave equipped with a double intermig stirrer and baffles. The reactor temperature was controlled by a Lauda Thermostat. The feed streams (solvents and monomers) were purified by contacting them with various absorption media as is known in the art. During polymerisation, the ethylene (C2) and propylene (C3) were continuously fed to the gas cap of the reactor. The pressure of the reactor was kept constant by means of a back-pressure valve.

Copolymerisation Experiments.

In an inert atmosphere of nitrogen, the reactor was filled with pentamethylheptanes (PMH) (950 mL) and an amount of MAO (Crompton 10 wt % in toluene) and 4-methyl-2,6-di-tert-butylphenol (BHT) as given in Tables 1 and 2. The reactor was heated to 90° C., while stirring at 1350 rpm. The reactor then was pressurized to 0.7 MPa and kept under a determined flow of 200 NL/h of ethylene and 400 NL/h of propylene for 15 minutes. Then, the catalyst components were added to the reactor and possible residual material was rinsed with PMH (50 mL) and subsequently fed to the reactor.

When tritylium tetrakis(perfluorophenyl)borate (TBF20) was used, the TBF20 was added directly after the catalyst was addition. After 10 minutes of polymerisation, the monomer flow was stopped and the solution was slowly poured into a 2 L Erlenmeyer flask, and dried over night at 100° C. under reduced pressure. The polymers were analysed by FT-IR to determine the amount of incorporated C3 and Intrinsic Viscosity being an indication for the average molecular weight.

Polymer Analysis.

The amount of incorporated C3 in weight per cents relative to the total composition, was measured by means of Fourier transformation infrared spectroscopy (FT-IR) according to ASTM D 3900 method A.

The Intrinsic Viscosity (IV) was measured at 135° C. in decaline.

EXAMPLES 1-16

In Situ Polymerisation

These catalysts were prepared in the polymerisation equipment by adding amounts as depicted in table 1a of toluene solutions of the metal-organic reagent, the ligand and the base successively to the catalyst dosing vessel in toluene (15 mL) and stirred during 5 minutes. From the catalyst dosing vessel the mixture was injected into the polymerisation reactor. Results are shown in Table 1b.

The experiments 1, 2, 5, 12 and 13 were carried by adding a prepared and purified metal-organic compound to the catalyst dosing vessel, and subsequently fed to the polymerisation reactor.

It can be concluded from the comparison of all experiments with experiment 2, that all in situ prepared catalysts produce copolymers having a higher molecular weight than the copolymer produced with the $CpTiCl_3$ only, which allows polymerisation of a polyolefin by just adding a metal-organic reagent, an imine ligand and at least 1 equivalent of a base to the polymerisation equipment.

From Examples 8 and 10 it can be concluded that a process in the presence of between 5 and 10 equivalents of the imine ligand according to formula 1 is mostly preferred.

TABLE 1a

In situ polymerisations: polymerisation conditions

| Example | Metal-organic reagent/ compound | Metal-organic compound dosage (µmol Ti) | ligand | Ligand dosage (µmol) | Base | Base dosage (µmol) | Activator system | Al/Ti Molar ratio | BF20/Ti Molar ratio | BHT/Al Molar ratio | Pol. Time (min) |
|---|---|---|---|---|---|---|---|---|---|---|---|
| 4 | CpTiCl3 | 0.4 | L1 | 0.8 | Et3N | 0.4 | MAO/BHT/ TBF20 | 3000 | 2 | 1 | 10 |
| 11 | CpTiCl3 | 0.4 | L2 | 2 | Et3N | 0.4 | MAO/BHT/ TBF20 | 3000 | 2 | 1 | 3 |

L1 = N,N,N',N',N'',N'',N''',N'''-hexamethylphosphorimidic triamide
L2 = 1,3-bis(2,6-dimethylphenyl)-iminoimidazoline TABLE 1b In situ polymerisations: polymerisation results

| Example | $\Delta T$ (°C.) | Yield (g) | residual Ti in polymer (ppm) | Incorporated C3 (wt %) | IV (dl/g) |
|---|---|---|---|---|---|
| 4 | 1.6 | 5.34 | 3.6 | 42 | Nd |
| 11 | 4.4 | 18.05 | 1.1 | 50 | |

The invention claimed is:

1. A process for the polymerization of at least one aliphatic $C_{2-20}$ or aromatic $C_{4-20}$ hydrocarbyl mono- or multiolefin in the presence of a catalyst and a boron comprising co-catalyst, wherein the catalyst comprises a composition of an organometallic reagent, a spectator ligand (SH) and optionally at least one equivalent of a hydrocarbylating agent, and the organometallic reagent is represented by $ML_jX_p$, wherein M is a metal from group 3-11, or the lanthanide series,
X is a monoanionic ligand bonded to M,
L is a neutral ligand bonded to M,
j represents an integer denoting the number of neutral ligands L, and
p is the valence of the metal M and
the spectator ligand is an imine ligand, or the HA adduct thereof, wherein HA represents an acid, of which H represents its proton and A its conjugate base.

2. A process for the polymerization of at least one aliphatic $C_{2-20}$ or aromatic $C_{4-20}$ hydrocarbyl mono- or multiolefin in the presence of a catalyst and a boron comprising co-catalyst, wherein the catalyst comprises a composition of an organometallic reagent, a spectator ligand (SH) and optionally at least one equivalent of a hydrocarbylating agent, and the organometallic reagent is represented by $ML_jX_p$, wherein M is a metal from group 3-11, or the lanthanide series,
X is a monoanionic ligand bonded to M,
L is a neutral ligand bonded to M,
j represents an integer denoting the number of neutral ligands L, and
p is the valence of the metal M,
and the spectator ligand is represented by:

$(HA_1)_q$-$Z_n$-$(A_2H)_r$, wherein
$A_1$ and $A_2$ are cyclopentadienyl comprising ligands,
q and r represent an integer denoting the number of Cp ligands with q+r=1 or 2, optionally linked by n parallel bridging groups Z, $A_1$, $A_2$ separately, or bonded via Z together forming a bidentate diacidic spectator ligand, and
n is 1, 2 or 3.

3. A process for the polymerization of at least one aliphatic $C_{2-20}$ or aromatic $C_{4-20}$ hydrocarbyl mono- or multiolefin in the presence of a catalyst and a boron comprising co-catalyst, wherein the catalyst comprises a composition of an organometallic reagent, a spectator ligand (SH) end optionally at least one equivalent of a hydrocarbylating agent, and the organometallic reagent is represented by $ML_jX_p$, wherein M is a metal from group 3-11, or the lanthanide series,
X is a monoanionic ligand bonded to M,
L is a neutral ligand bonded to M,
j represents an integer denoting the number of neutral ligands L, and
p is the valence of the metal M
and the spectator ligand is a ligand according to the formula:

$HA_1$-Z-$D(H)_b$, in which
$A_1$ is a delocalized $\eta^5$ bonding cyclopentadienyl comprising ligand,
Z is a moiety comprising boron, or a member of Group 14, and optionally also sulfur or oxygen, said moiety having up to 20 non-hydrogen atoms, and optionally $A_1$ and Z together form a fused ring system,
D is a Lewis basic ligand bonded to Z, comprising a group 15 or 16 atoms and having up to 20 non-hydrogen atoms, or optionally D and Z together form a fused ring system and
b=0 or 1.

4. A process for the polymerization of at least one aliphatic $C_{2-20}$ or aromatic $C_{4-20}$ hydrocarbyl mono- or multiolefin in the presence of a catalyst and a boron comprising co-catalyst, wherein the catalyst comprises a composition of an organometallic reagent a spectator ligand (SH) and optionally at least one equivalent of a hydrocarbylating agent, and the organometallic reagent is represented by $ML_jX_p$, wherein M is a metal from group 3-11, or the lanthanide series,
X is a monoanionic ligand bonded to M,
L is a neutral ligand bonded to M,
j represents an integer denoting the number of neutral ligands L, and
p is the valence of the metal M and
the spectator ligand is represented by:

$Y(-R-DR'_n)_q$, in which
- Y represents a (substituted) cyclopentadienyl, (substituted) indenyl, (substituted) fluorenyl, (substituted) heterocyclopentadienyl, (substituted) heteroindenyl, (substituted) heterofluorenyl, or an imine group,
- R is an optional bridging group between the Y moiety and the $DR'_n$,
- D is a hetero atom selected from group 15 or 16,
- R' is an optional substituent,
- n is the number of R' groups bonded to D and is 1 or 2, and
- q is an integer >1.

5. A process for the polymerization of at least one aliphatic $C_{2-20}$ or aromatic $C_{4-20}$ hydrocarbyl mono- or multiolefin in the presence of a catalyst and a boron comprising co-catalyst, wherein the catalyst comprises a composition of an organometallic reagent, a spectator ligand (SH) and optionally at least one equivalent of a hydrocarbylating agent, and the organometallic reagent is represented by $ML_jX_p$, wherein
- M is a metal from group 3-11, or the lanthanide series,
- X is a monoanionic ligand bonded to M,
- L is a neutral ligand bonded to M,
- j represents an integer denoting the number of neutral ligands L, and
- p is the valence of the metal M and the ligand is represented by

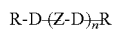

$R-D-(Z-D)_n-R$ wherein
- Z is a bridging group, between two donor atom containing groups (D),
- D is a group comprising a hetero atom chosen from group 15 or 16,
- n is 0, 1, 2 or 3, and
- R is a substituent and wherein the metal is a metal from Group 7-11.

6. The process according to any of claims 1 to 5, wherein the hydrocarbylating agent comprises a metal or a metalloid chosen from group 1, 2, 11, 12, 13 or 14.

7. The process according to claim 6, wherein the hydrocarbylating agent comprises Li, Mg, Zn, or Al.

8. The process according to claim 7, wherein the hydrocarbylating agent is a $C_1$-$C_{20}$ trihydrocarbyl aluminum or aluminoxane.

9. The process according to any of claims 1 to 5, carried out the presence of a base other than the hydrocarbylating agent.

10. The process according to claim 1, wherein the organometallic reagent comprises a group 4 metal and a cyclopentadienyl-comprising ligand.

11. The process according to claim 2 or 3, wherein the metal is a group 4 or group 5 metal, or a metal selected from the lanthanide series.

12. The process according to claim 4, wherein the metal is a group 4 metal with a valency of 3.

* * * * *